United States Patent [19]

Barth

[11] Patent Number: 5,622,716
[45] Date of Patent: Apr. 22, 1997

[54] PROCESS FOR PREPARING A RETARD PRODUCT CONTAINING DILTIAZEM FOR A SINGLE DAILY ADMINISTRATION

[75] Inventor: Dieter Barth, Erbach, Germany

[73] Assignee: Farmarc Nederland B.V., Amsterdam, Netherlands

[21] Appl. No.: 636,686

[22] Filed: Apr. 23, 1996

Related U.S. Application Data

[63] Continuation of Ser. No. 145,022, Oct. 27, 1993, abandoned, which is a continuation of Ser. No. 853,885, Mar. 18, 1992, abandoned, which is a continuation of Ser. No. 500,025, Mar. 26, 1990, abandoned, which is a continuation-in-part of Ser. No. 156,829, Feb. 17, 1988, abandoned.

[30] Foreign Application Priority Data

Feb. 20, 1987 [CH] Switzerland .................... 00637/87

[51] Int. Cl.$^6$ .................................................. A61K 9/62
[52] U.S. Cl. .................... 424/461; 424/456; 424/462; 424/493; 424/494; 424/495; 424/496; 424/497; 424/498
[58] Field of Search ...................... 424/461, 462, 424/471, 479, 480, 482, 494–497

[56] References Cited

U.S. PATENT DOCUMENTS

| | | | |
|---|---|---|---|
| 3,782,993 | 1/1974 | Rothgang | 424/497 |
| 4,721,619 | 1/1988 | Panoz et al. | 424/490 X |
| 4,871,731 | 10/1989 | Walker | 514/211 |
| 4,891,230 | 1/1990 | Geoghegan et al | 424/494 X |
| 4,917,899 | 4/1990 | Geoghegan et al. | 424/461 |

*Primary Examiner*—Neil Levy

[57] ABSTRACT

This invention is directed towards pellets and a process for manufacturing pellets of diltiazem HCl having a dissolution kinetic independent from pH.

4 Claims, 15 Drawing Sheets

IN-VITRO RELEASE CURVES OF DILTIAZEM HC1( MARION LOT T 8745 ) 120 mg/cps AT DIFFERENT pH VALUES ( USP XXI PADDLE 60 rpm )

PROCESS FOR PREPARING A RETARD PRODUCT CONTAINING DILTIAZEM FOR A SINGLE DAILY ADMINISTRATION

This application is a continuation of application No. 08/145,022, filed Oct. 27, 1993, now abandoned, which is a continuation of application No. 07/853,885, filed Mar. 18, 1992, now abandoned, which is a continuation of application(s) Ser. No. 07/500,025 filed on Mar. 26, 1990, now abandoned, is a continuation in part of now abandoned U.S. application 156,829, filed on Feb. 17, 1988.

FIELD OF THE INVENTION

This invention is directed towards pellets and a process for manufacturing pellets of diltiazem HCl having a dissolution kinetic independent from pH.

BACKGROUND OF THE INVENTION

Diltiazem, 3-(acetyloxy)-5-[2-(dimethylamino)-ethyl]-2,3-dihydro-2- (4-metoxyphenyl)-1,5-benzotiazepin-4 (5H)-one acetate, is efficacious in angina and hypertension. It is normally used as hydrochloride.

Diltiazem HCl is a white crystalline powder, freely soluble in water. Because of its physico-chemical characteristics, diltiazem is a substance with a pH-dependent solubility.

An oral modified-release pharmaceutical form of diltiazem should exhibit a kinetic of dissolution suitable to ensure blood levels of the drug therapeutically efficacious for the entire time between two subsequent administrations.

Few aspects are of great importance to make the drug-product safe and effective under all the physiological circumstances:

reproducibility of bio pharmaceutical behaviors from batch to batch, rate of dissolution largely pH-independent, rate of dissolution largely motility-independent, rate of dissolution independent from food-intake.

Among the already marketed modified-release products, not all match the above-mentioned requirements.

In-vitro dissolution checks show, in the range of pH between 1 and 7.5, a sharp increase of the release at neutral pH (FIG. 1).

Since the solubility of diltiazem is lower at neutral pH, compared to acidic pH, the observed behavior suggests that in the examined product diltiazem is released by diffusion through an insoluble polymer film, as long as the pH is lower than 7, and by desegregation of the formulation at higher pHs.

A formulation with characteristics as above, in presence of g.i. transit times ranging from few to many hours, may give rise to dose dumping.

SUMMARY OF THE INVENTION

It is an object of the invention to provide a pellet containing diltiazem HCl having a dissolution kinetic independent of the pH of the environment.

It is a further object of the invention to provide pellets containing diltiazem HCl.

DETAILED DESCRIPTION OF THE PREFERRED EMBODIMENTS OF THE INVENTION

Previously filed U.S. patent application 156,829 (now abandoned) describes the preparation of modified-release pellets of diltiazem HCl by means of the well-known coating pan method and exhibiting the release rate of diltiazem HCl driven by diffusion through a polymer film, according to the following relation:

$$\text{Rate} = \frac{A \times D \times K \times \Delta C}{L}$$

where:

A=surface exposed to diffusion

D=diffusivity

K=partition coefficient between inside of the pellet

C=concentration gradient between inside of the pellet and external environment.

Letting the concentrations of the environment be equal to zero, as in the case of sink conditions, the dissolution rate is determined to be the concentration of the drug into the pellet.

It becomes obvious that in the case of diltiazem HCl, its solubility decreases when pH increases, Thus when increasing the pH, the concentration of the saturated solution of diltiazem in the pellets will decrease, and consequently the release rate will decrease.

Figure 1:
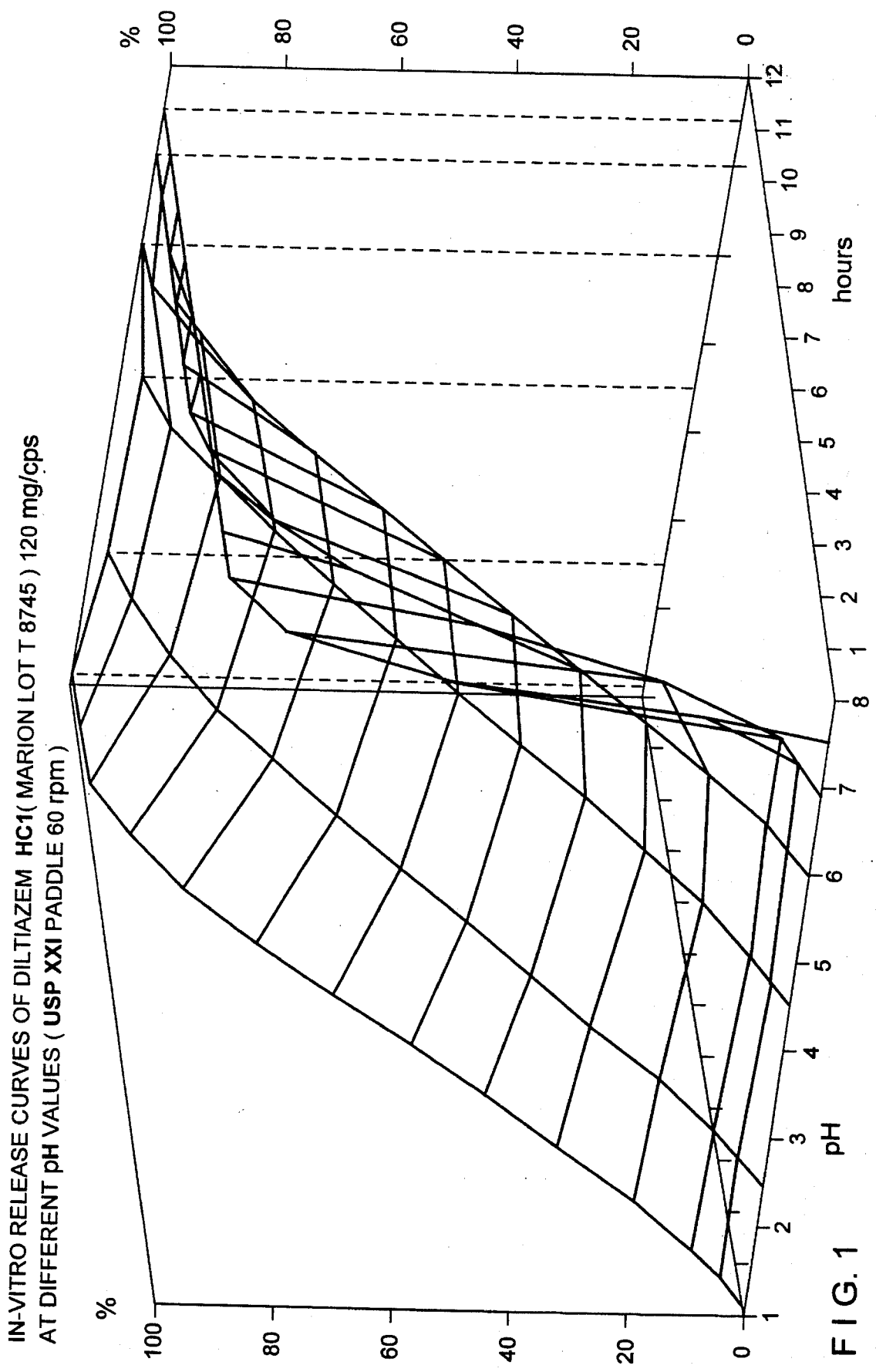
FIG. 1 is a graphical representation of the in-vitro release of diltiazem hydrochloride at different Ph values in accord with the prior art.
Figure 2:
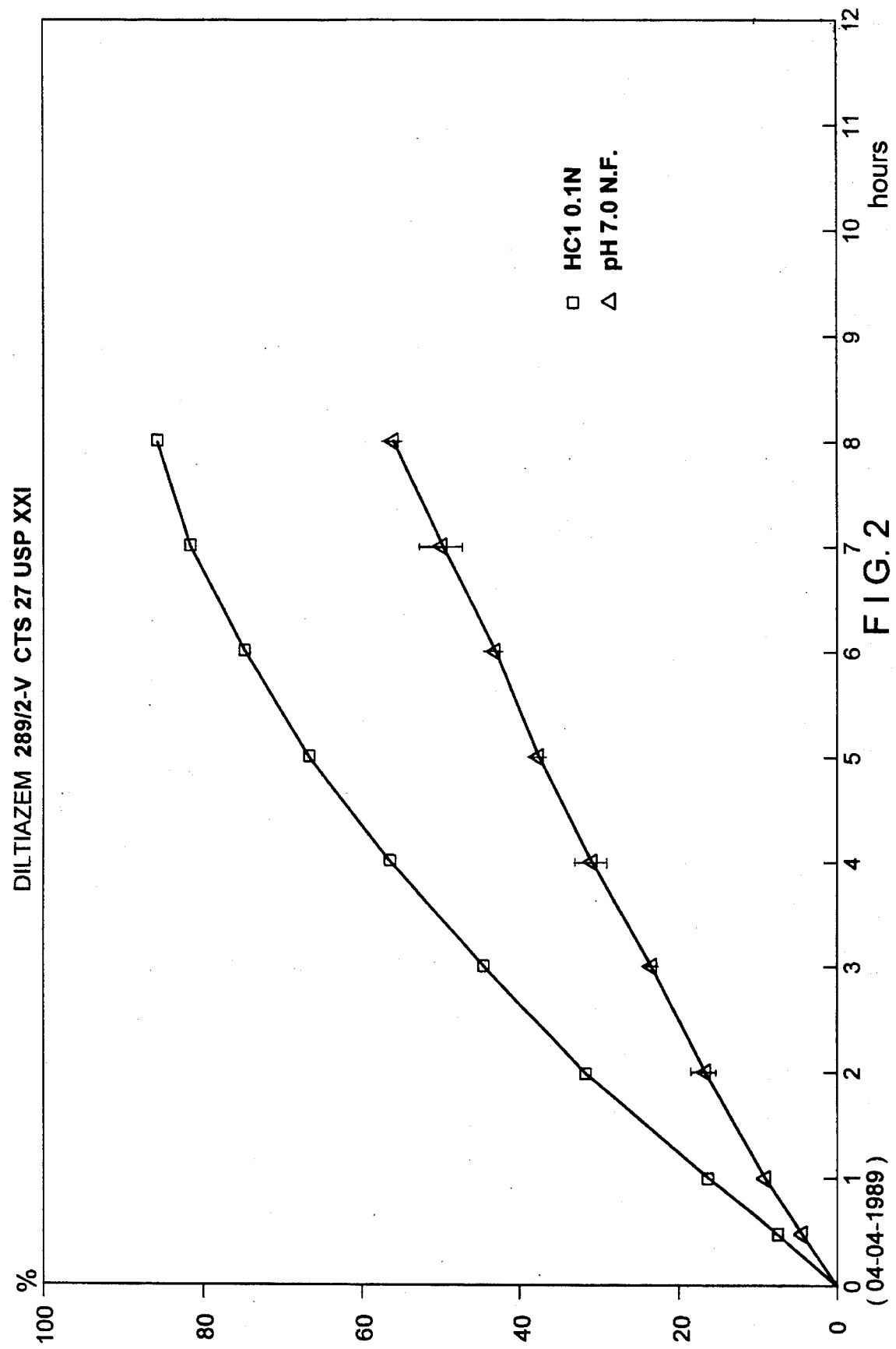
FIG. 2 is a graphical representation of the solubility of diltiazem hydrochloride plotted to compare against different Ph values.

FIG. 2 shows the above described effect relevant to the formulation prepared according to the example C.2 in the U.S. patent application 156,829 described above.

The example C.2 recites the following:

C.2 DILTIAZEM DELAYED-RELEASE PELLETS

The quantity of pellets obtained (point C.1) is rotated in a trough 450 mm in diameter, and bathed with 80 g of a sprayed 5% strength solution of Ethoxyl N 100 in acetone/ethanol and sprinkled with 54 g of talc. The spraying and sprinkling operation is alternated and is repeated 25 times in total.

Point C.1 referred to above, recites:

C.1 DILTIAZEM RAPID-RELEASE PELLETS 2.00 kg of microgranules composed of succrose and starch, with a particle size of 0.500–0.710 mm, are rotated in a trough with a stainless steel basket 450 mm in diameter. The rotating mass is sprayed, by means of a membrane-type proportioning pump, with 26 g of a 40% strength solution of shellac in ethanol and sprinkled with 80 g of diltiazem with a particle size of 40–80 microns.

Figure 15:
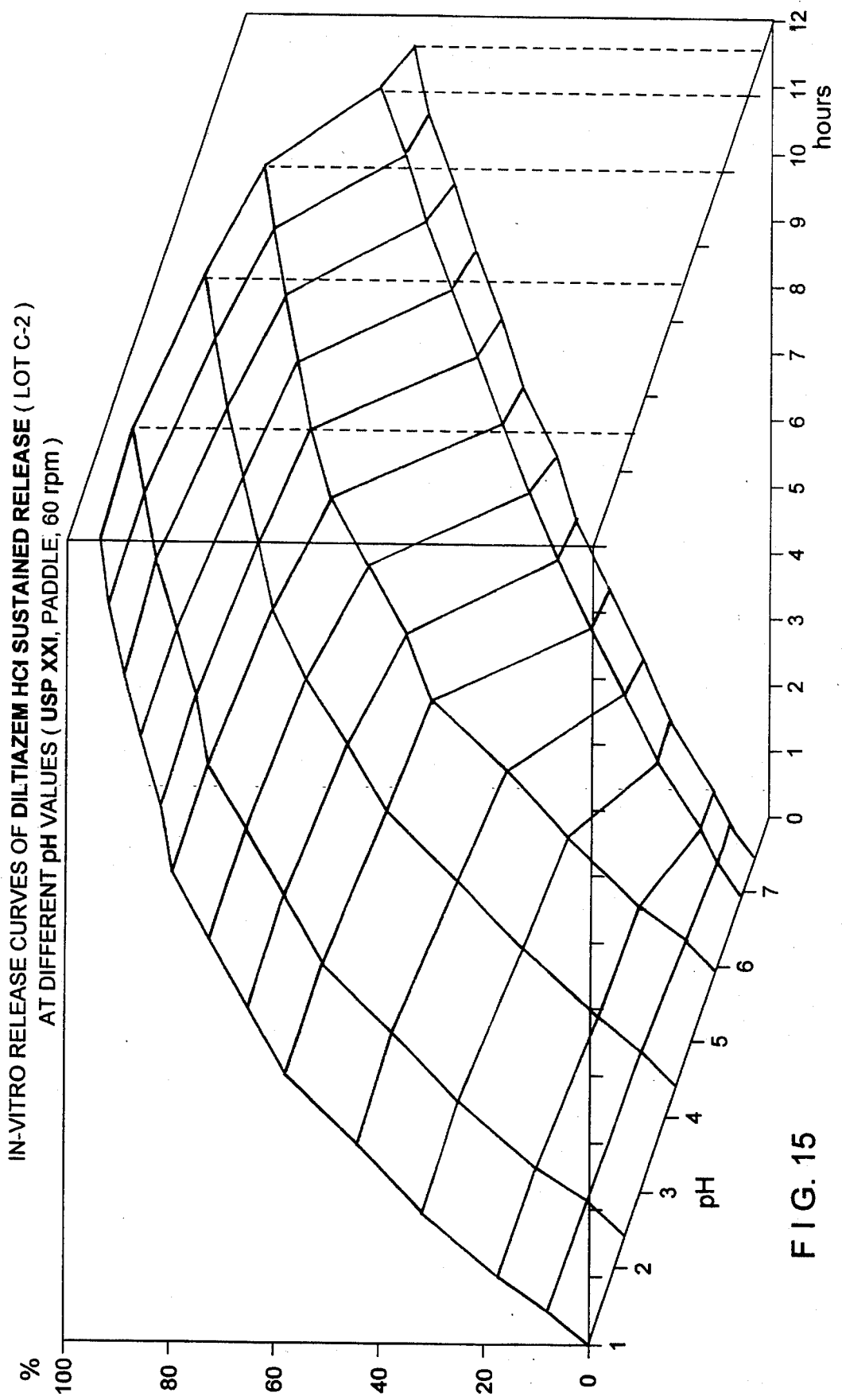
FIG. 15 is a graphical representation of an in-vitro release rate at different Ph values, determined for the experimental formulation (a).

The spraying and sprinkling operation is alternated and repeating the spraying step in the range of 40 to 70 times. Release data at varying pH values is depicted in FIG. 15.

In order to avoid this inconvenience, a mixture of diltiazem HCl with organic acids has been used with the scope of buffering to an acidic pH the confined environment into the pellet, and so getting a higher concentration of diltiazem HCl into the saturated solution (E.P.A.-0149920-Elan).

High diltiazem concentration independent of the pH of the dissolution medium results in a rate of dissolution largely independent of pH.

Starting from the results of example C of U.S. patent application 156,829, we have introduced increasing amounts of substances with hydro-lipophilic properties in order to verify the co-solubilizing effect on diltiazem HCl in the confined environment of the inside of a pellet, coated with an insoluble polymer film having pure diffusive properties.

The following ingredients have been used:

polyvinylpyrrolidone polyethylenglycol methylcellulose.

Several samples have been prepared using mixtures in variable proportions of shellac and the above-mentioned ingredients.

The objective was to verify:

a) the influence of substances with hydro-lipophilic properties in increasing the solubility of diltiazem HCl at neutral pHs, b) the determine the optimal ratio between insoluble binder (shellac) and soluble binder, to get a kinetic of in-vitro release as independent as possible from pH and suitable to obtain sustained in-vivo therapeutical blood levels of diltiazem suitable for administration of one dose every 24 hours.

The medication can be provided in the form of solid, oral form, gelatin capsules.

Figure 3:
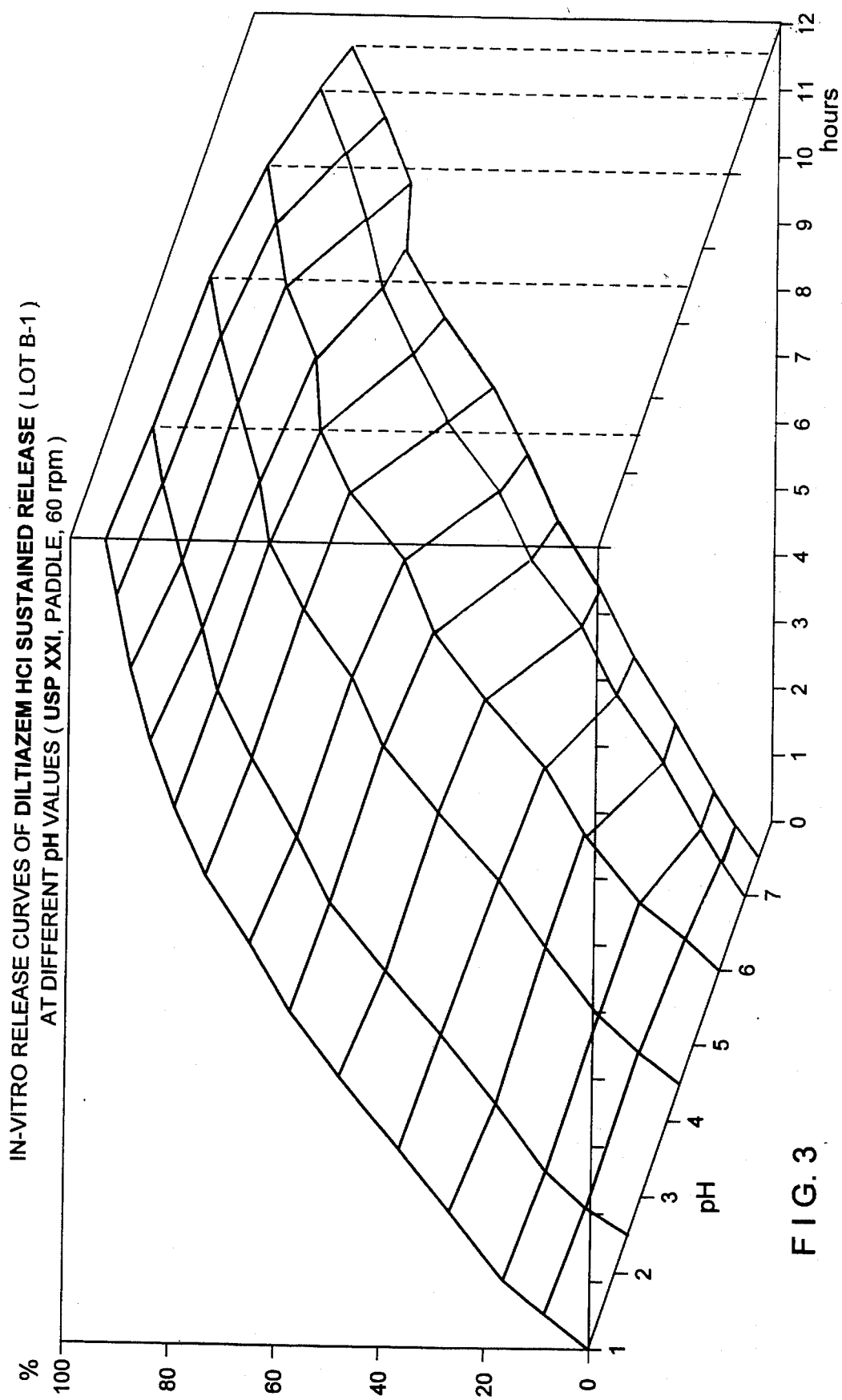
FIGS. 3–14, inclusive, are each graphical representations of in-vitro release rates at different Ph values, determined for the experimental formulations (b. 1)-(b. 12), respectively.
Figure 4:
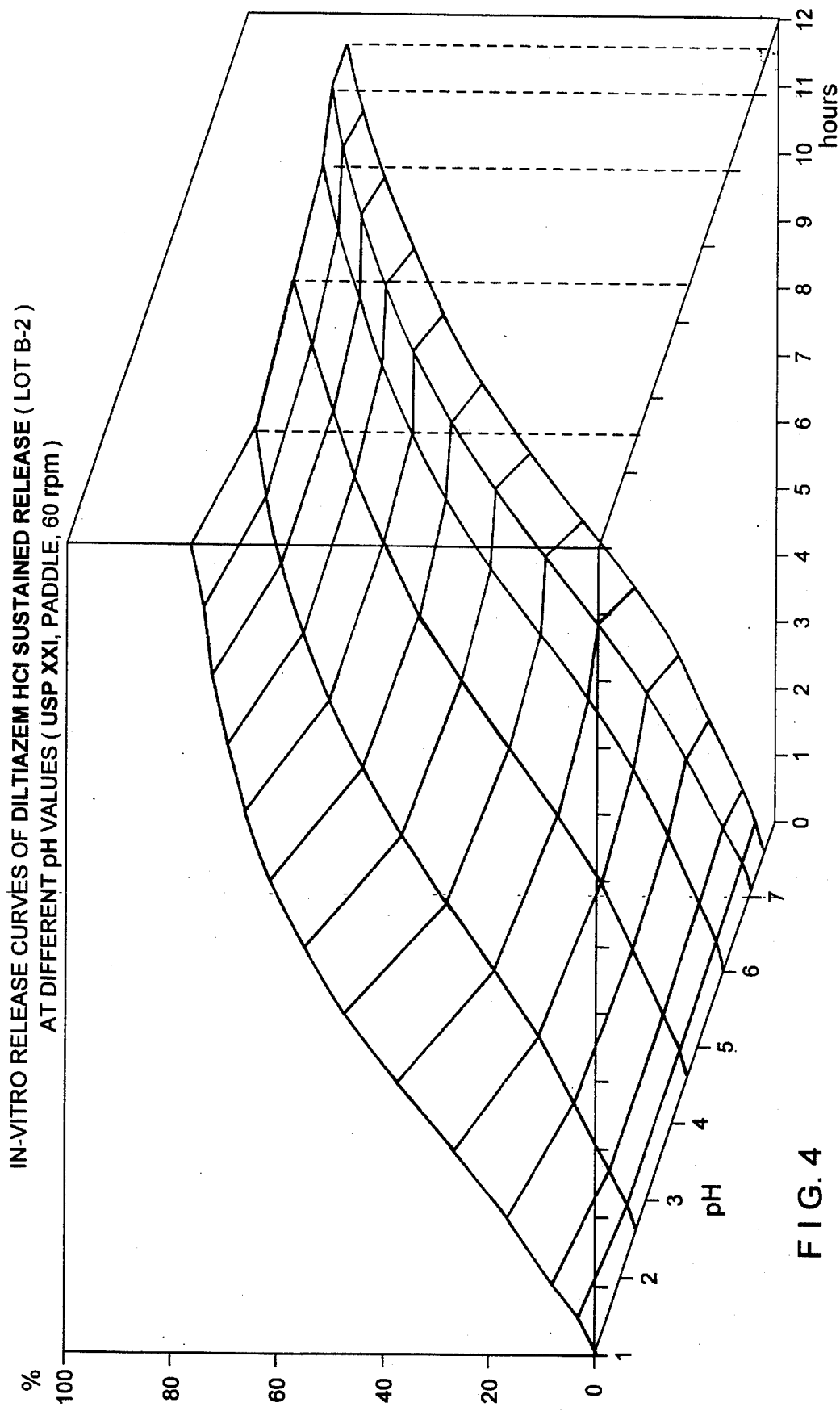
Figure 5:
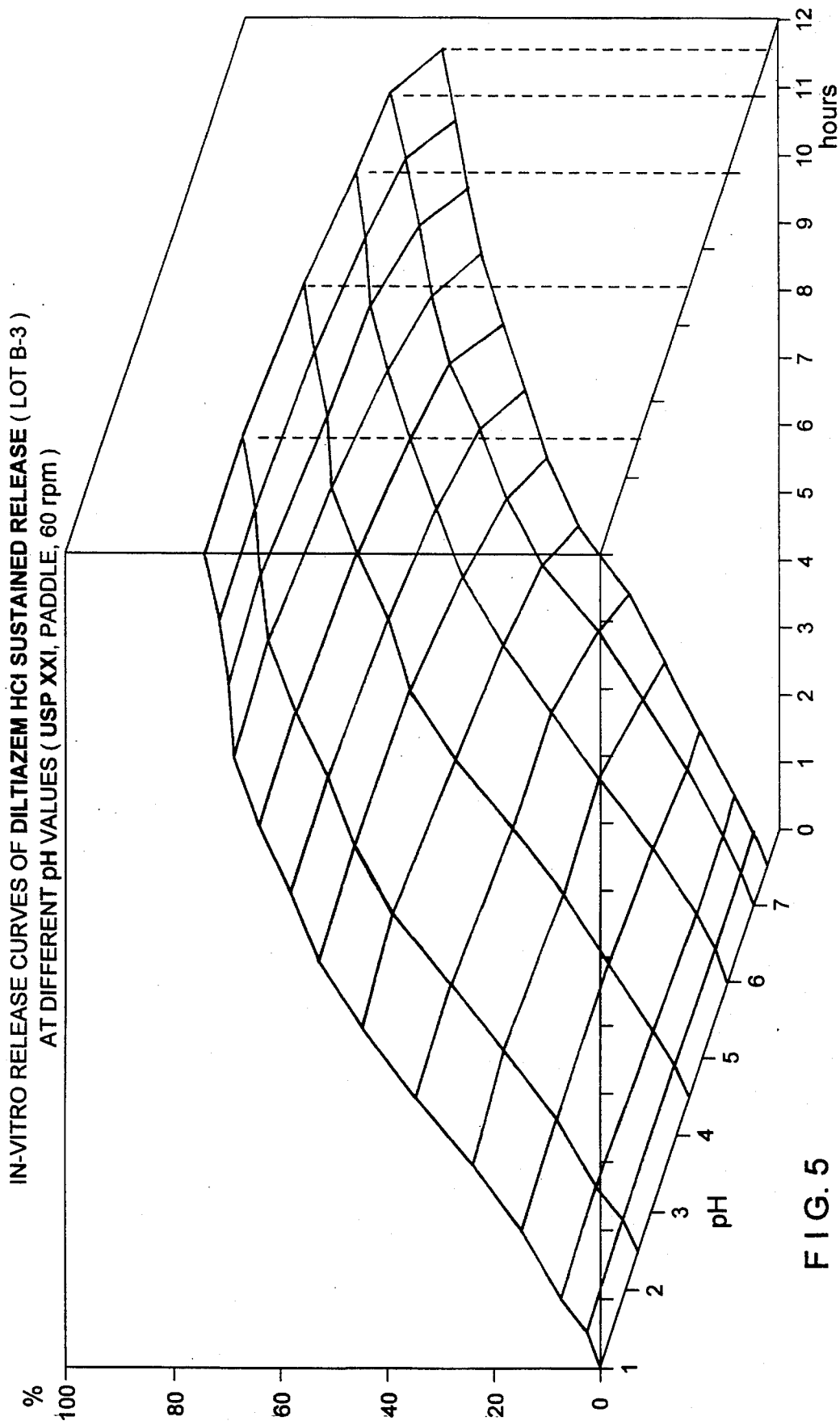
Figure 6:
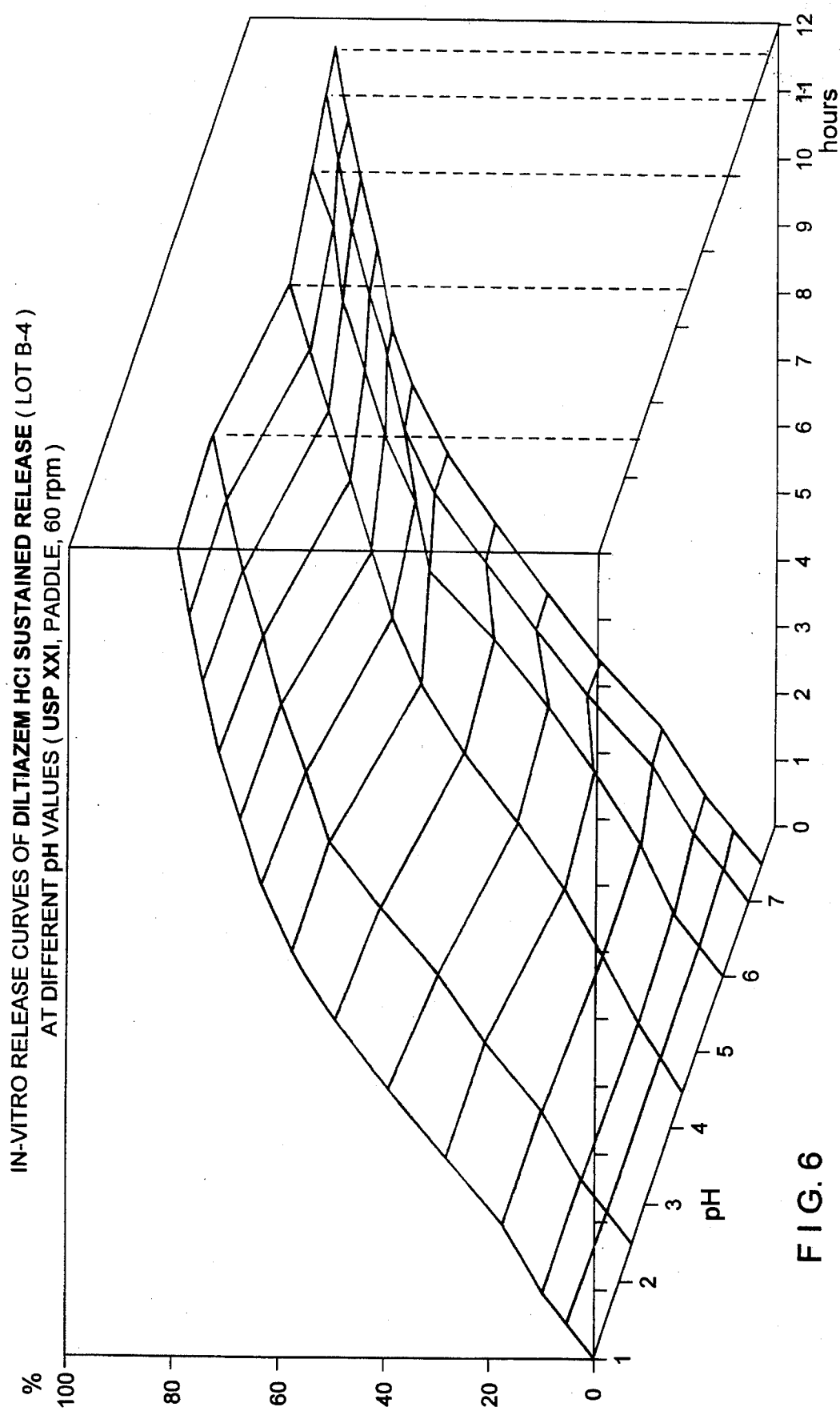
Figure 7:
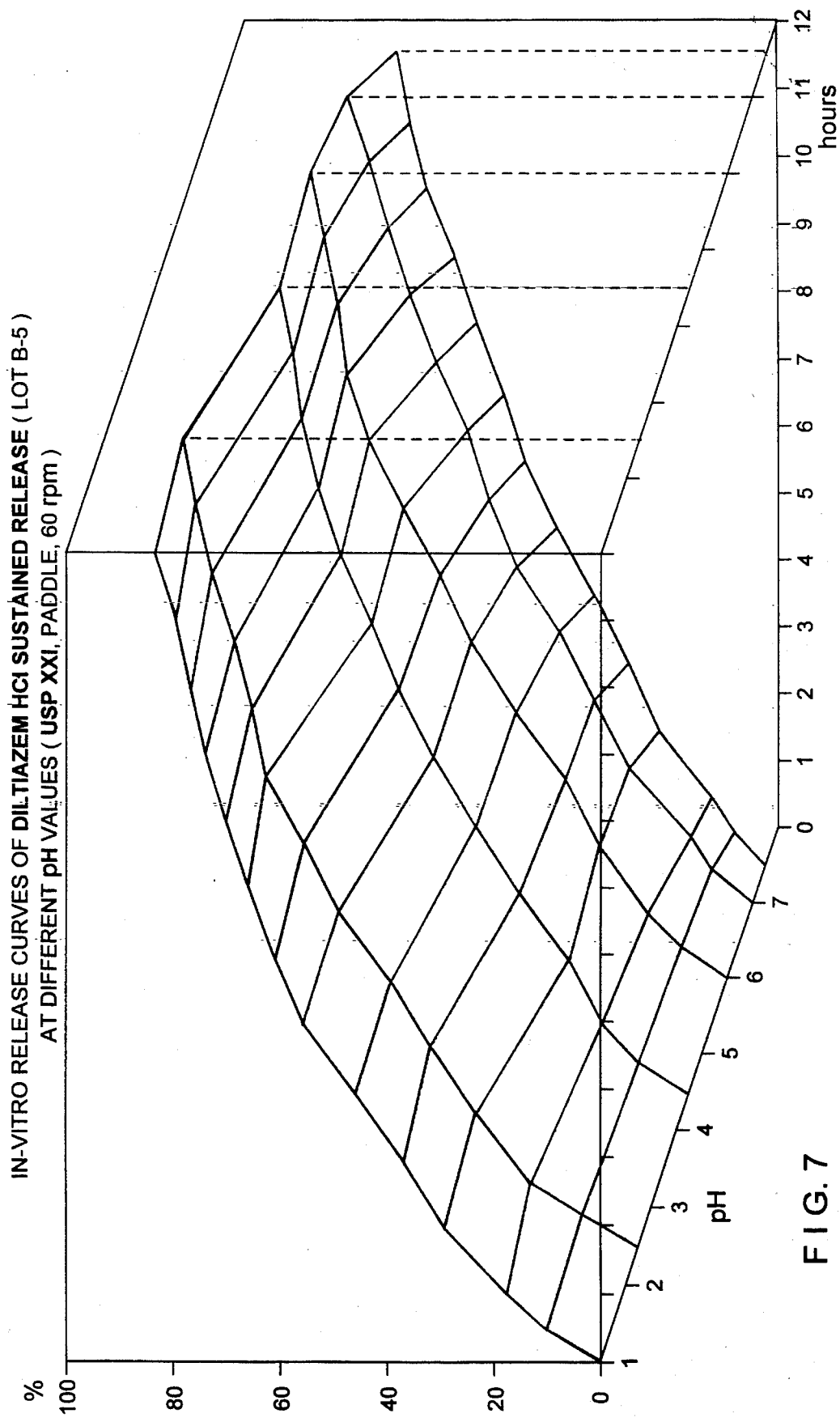
Figure 8:
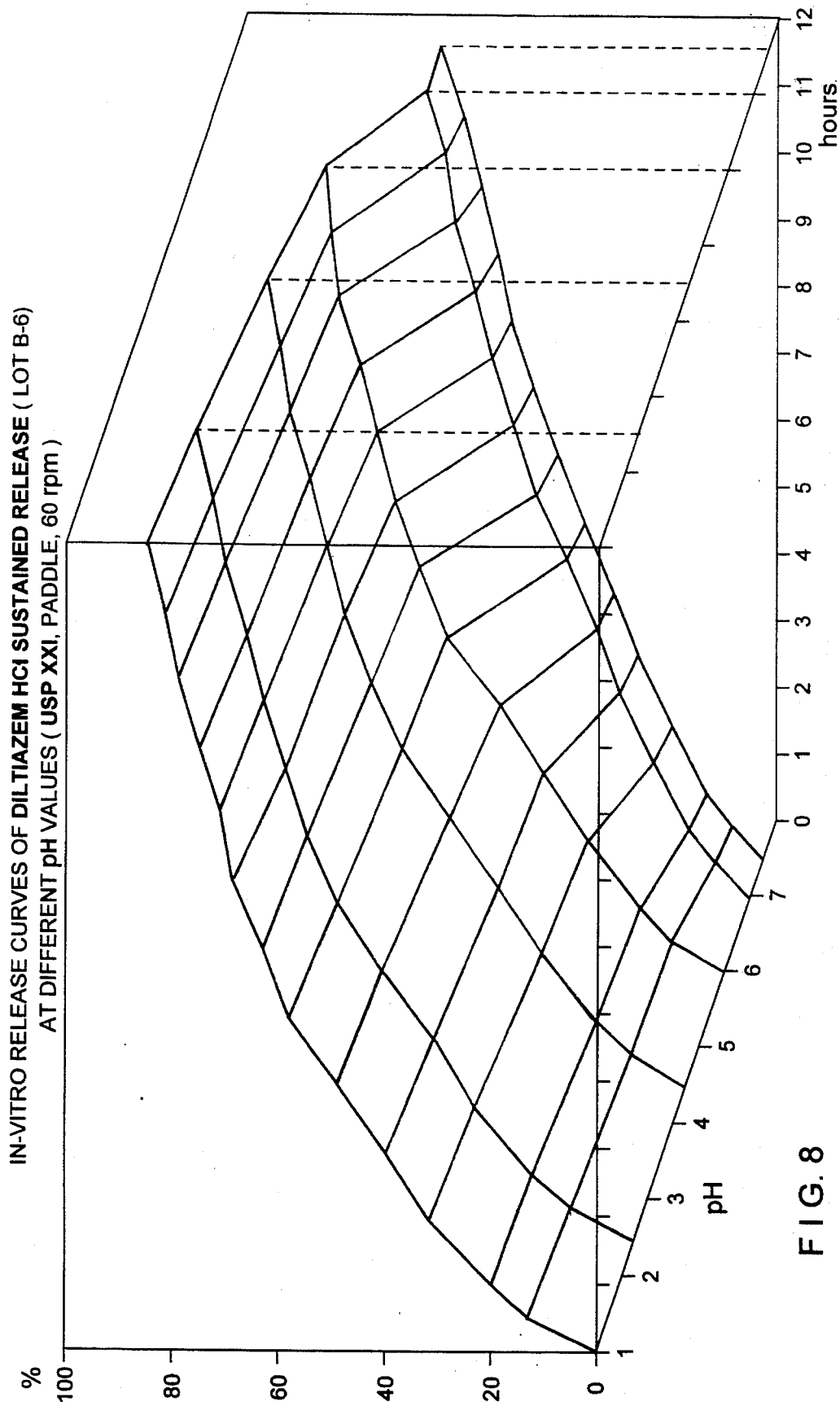
Figure 9:
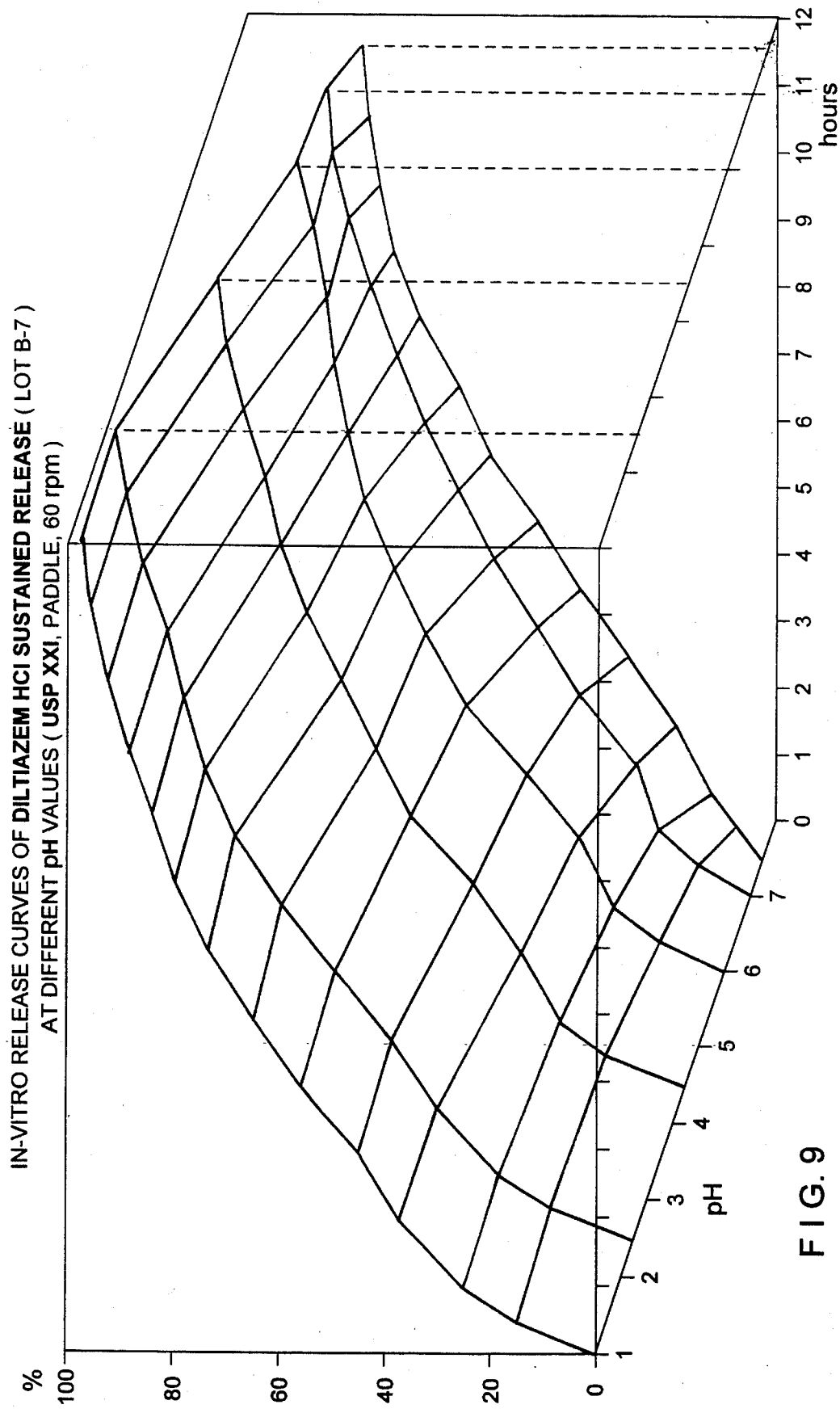
Figure 10:
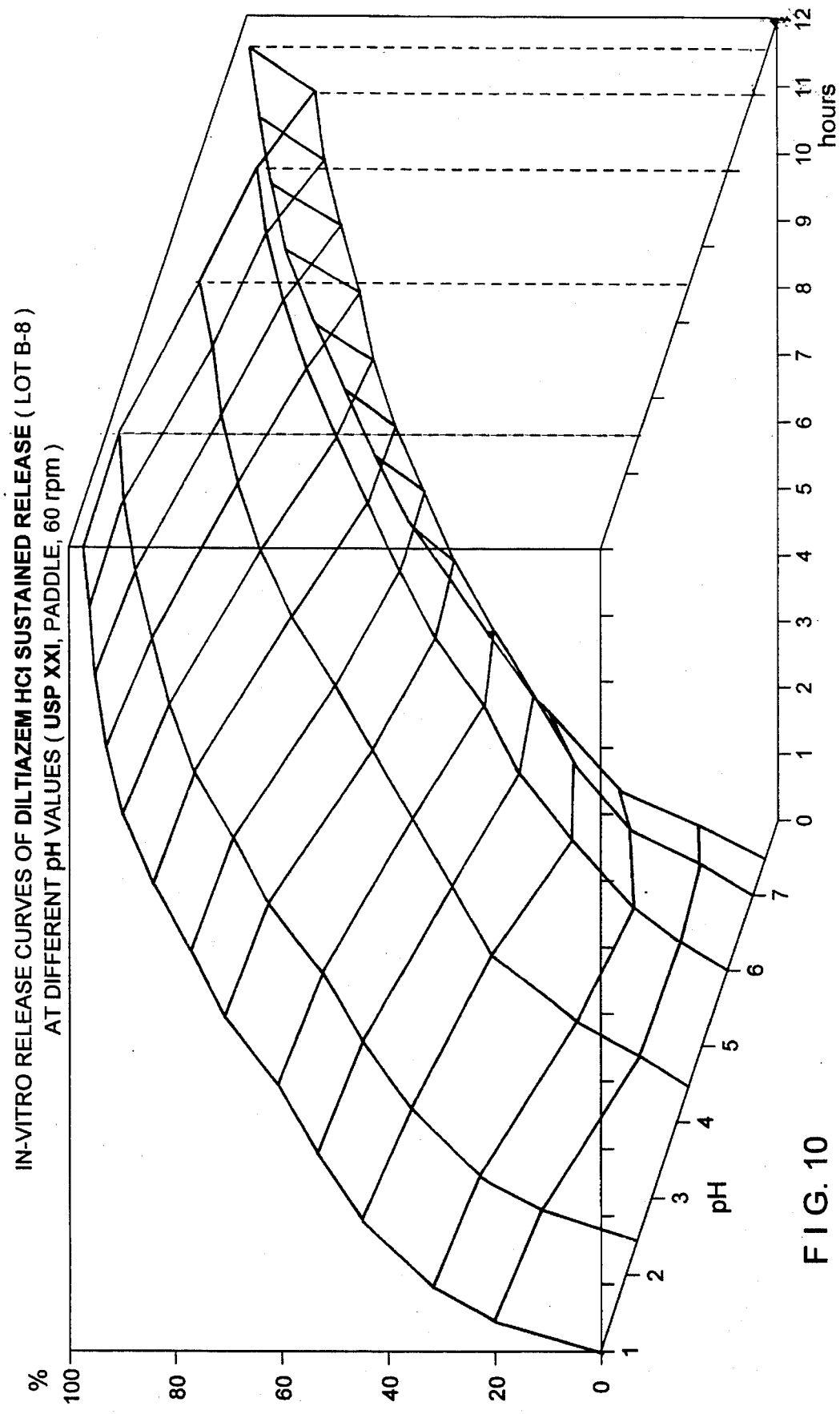
Figure 11:
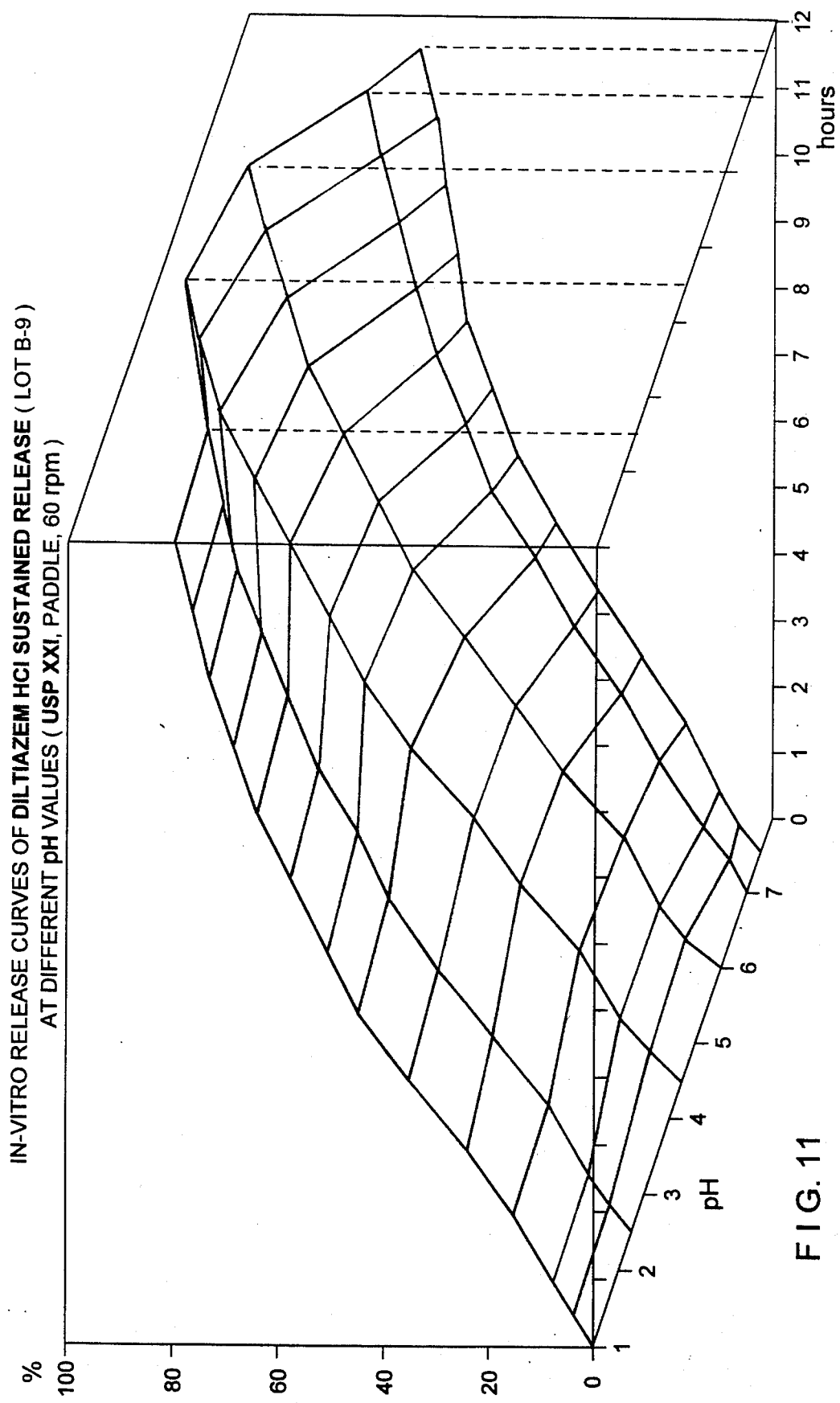
Figure 12:
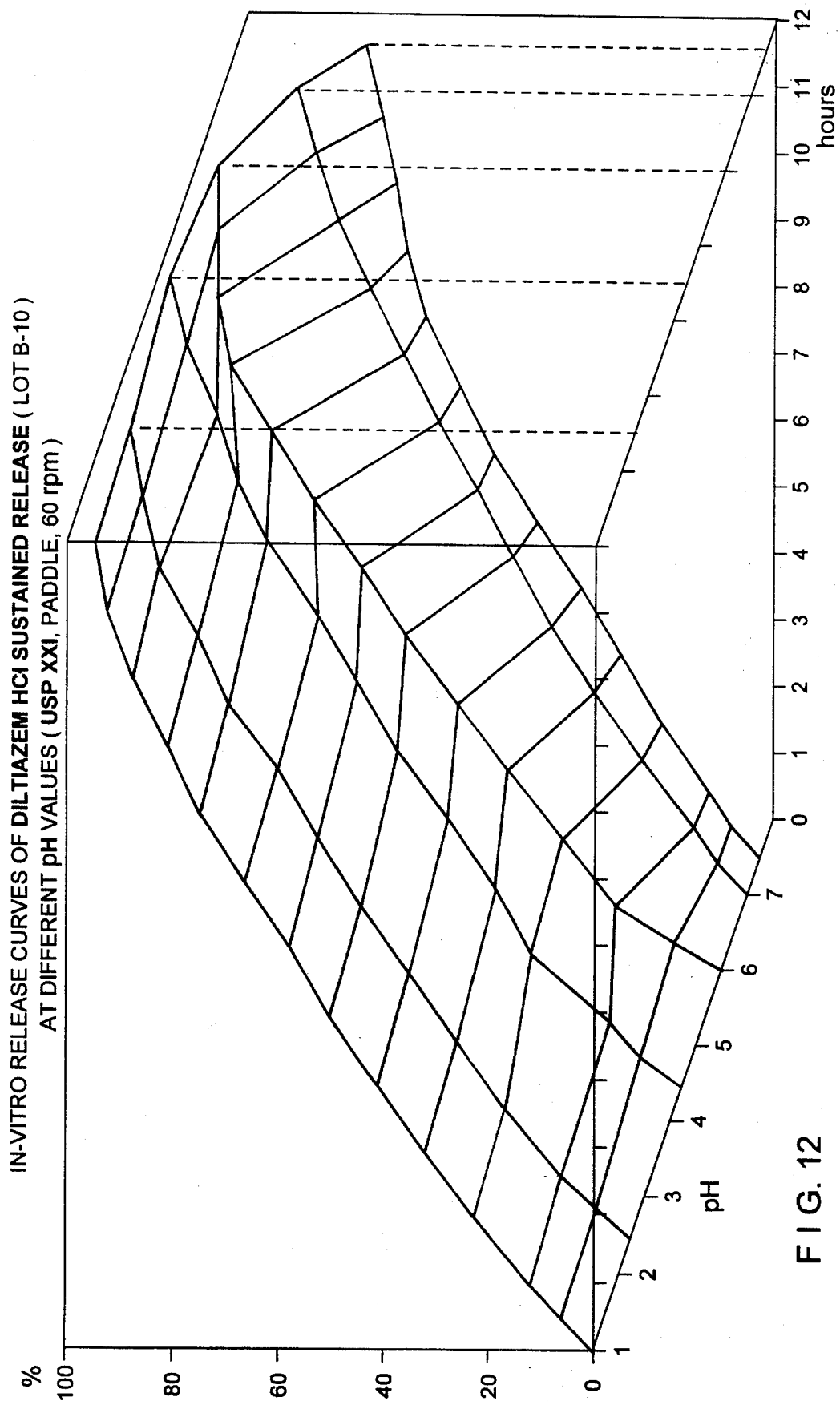
Figure 13:
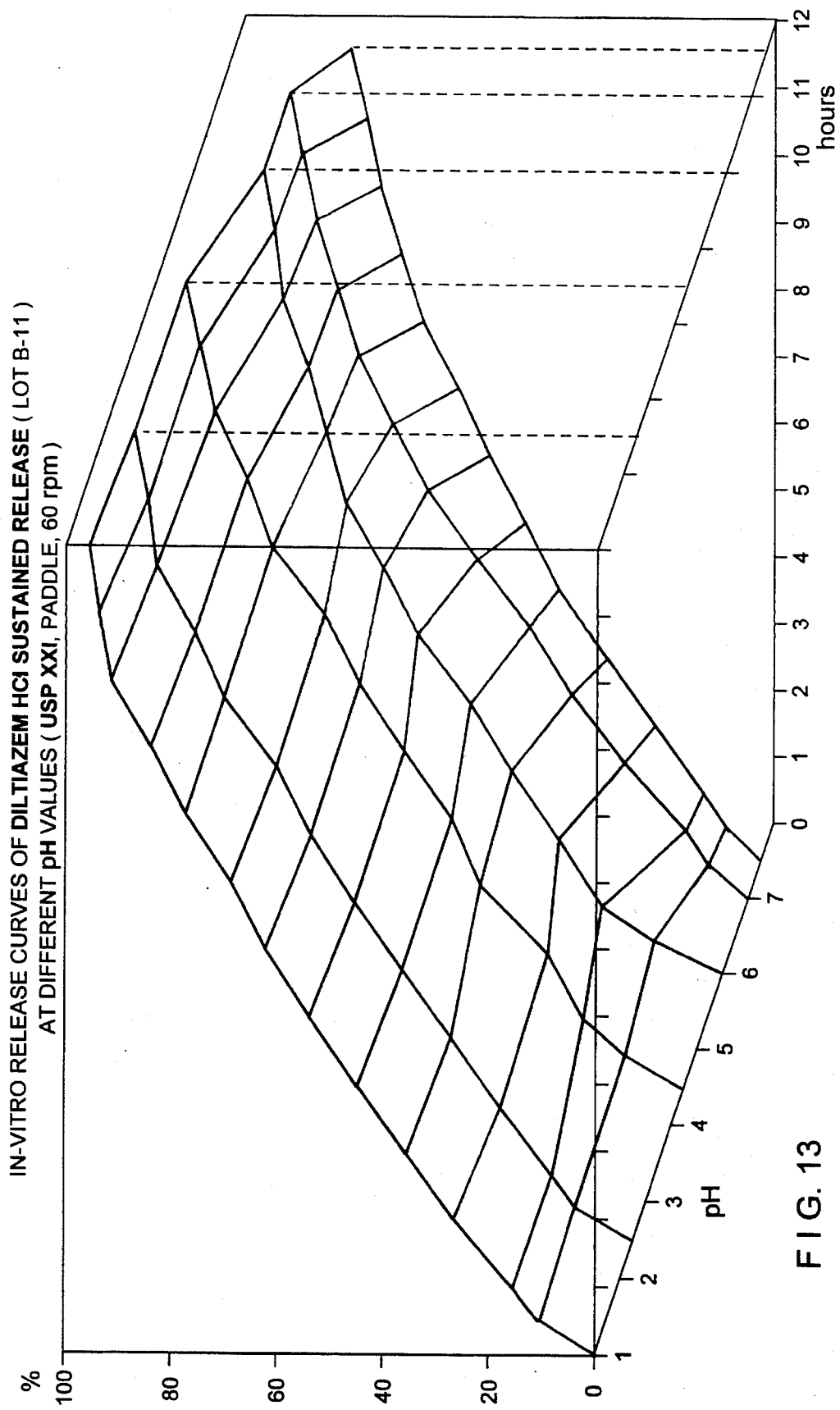
Figure 14:
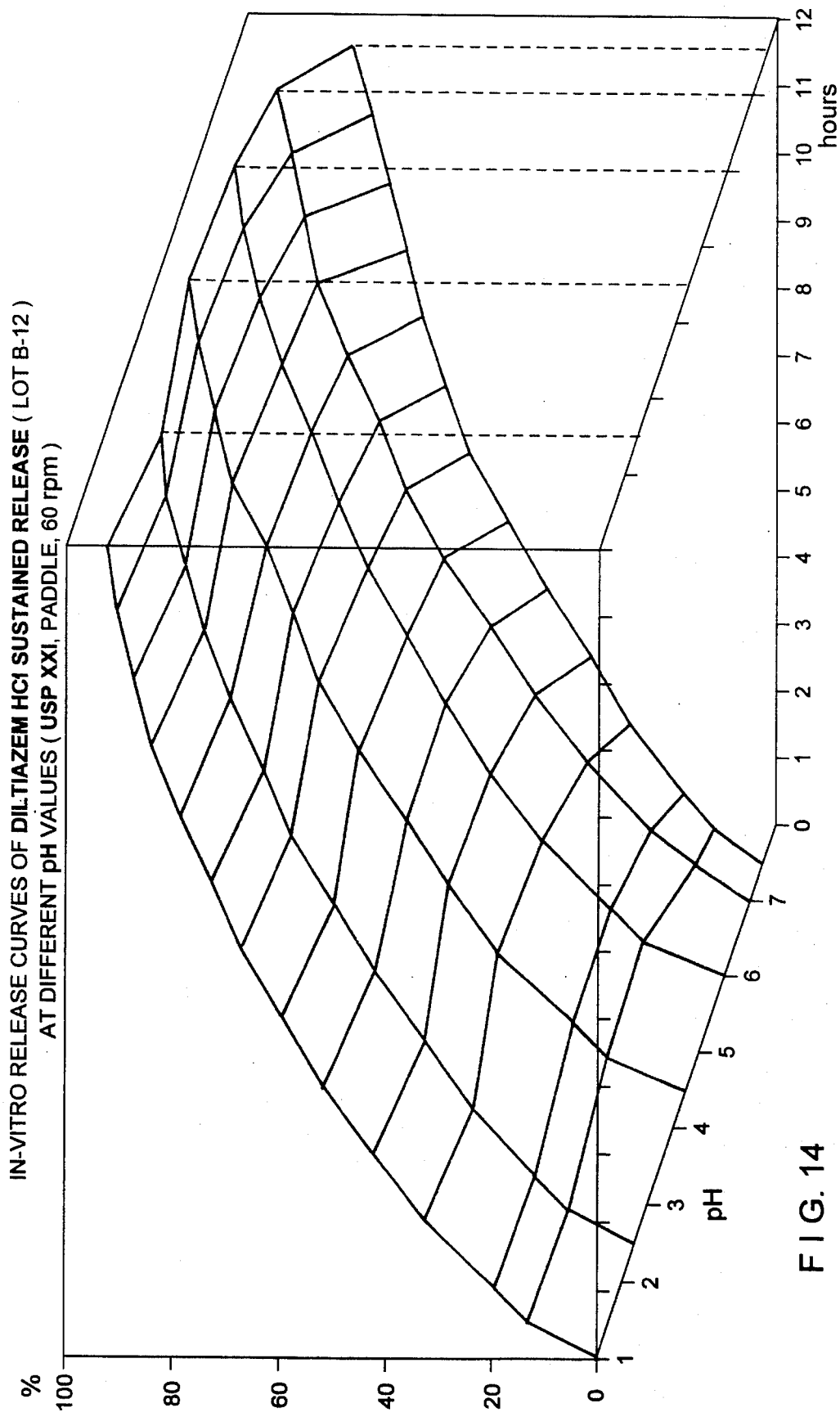

EXPERIMENTAL a) Reference formulation: as described in example C of U.S. patent application 156,829 set forth above. See FIG. 15.

b) Experimental formulations:

b.1) 2.00 kg of saccharose/starch pellets having a particle size between 0.500 and 0.710 mm are put in rotation in a suitable coating pan. The rotating mass is sprayed with 27.2 g of an ethanolic solution containing 9.79 g of shellac and 1.09 g of polyvinylpyrrolidone and 80 g of diltiazem HCl are added. This operation is repeated 50 times. Release data at varying pH values is shown in FIG. 3.

b.2) 2.00 kg of saccharose/starch pellets having a particle size between 0.500 and 0.710 mm are put in rotation in a suitable coating pan. The rotating mass is sprayed with 27.2 g of an ethanolic solution containing 7.62 g of shellac and 3.26 g of polyvinylpyrrolidone and 80 g of diltiazem HCl are added. This operation is repeated 50 times. Release data at varying pH values is shown in FIG. 4.

b.3) 2.00 kg of saccharose/starch pellets having a particle size between 0.500 and 0.710 mm are put in rotation in a suitable coating pan. The rotating mass is sprayed with 27.2 g of an ethanolic solution containing 5.44 g of shellac and 5.44 g of polyvinylpyrrolidone and 80 g of diltiazem HCl are added. This operation is repeated 50 times. Release data at varying pH values is shown in FIG. 5.

b.4) 2.00 kg of saccharose/starch pellets having a particle size between 0.500 and 0.710 mm are put in rotation in a suitable coating pan. The rotating mass is sprayed with 27.2 g of an ethanolic solution containing 3.26 g of shellac and 7.62 g of polyvinylpyrrolidone and 80 g of diltiazem HCl are added. This operation is repeated 50 times. Release date at varying pH values is shown in FIG. 6.

b.5) 2.00 kg of saccharose/starch pellets having a particle size between 0.500 and 0.710 mm are put in rotation in a suitable coating pan. The rotating mass is sprayed with 27.2 g of an ethanolic solution containing 9.79 g of shellac and 1.09 g of polyethyleneglycol and 80 g of diltiazem HCl are added. This operation is repeated 50 times. Release data at varying pH values is shown in FIG. 7.

b.6) 2.00 kg of saccharose/starch pellets having a particle size between 0.500 and 0.710 mm are put in rotation in a suitable coating pan. The rotating mass is sprayed with 27.2 g of an ethanolic solution containing 7.62 g of shellac and 3.26 g of polyethyleneglycol and 80 g of diltiazem HCl are added. This operation is repeated 50 times. Release data at varying pH values is shown in FIG. 8.

b.7) 2.00 kg of saccharose/starch pellets having a particle size between 0.500 and 0.710 mm are put in rotation in a suitable coating pan. The rotating mass is sprayed with 27.2 g of an ethanolic solution containing 5.44 g of shellac and 5.44 g of polyethyleneglycol and 80 g of diltiazem HCl are added. This operation is repeated 50 times. Release data at varying pH values is shown in FIG. 9.

b.8) 2.00 kg of saccharose/starch pellets having a particle size between 0.500 and 0.710 mm are put in rotation in a suitable coating pan. The rotating mass is sprayed with 27.2 g of an ethanolic solution containing 3.26 g of shellac and 7.62 g of polyethyleneglycol and 80 g of diltiazem HCl are added. This operation is repeated 50 times. Release data at varying pH values is shown in FIG. 10.

b.9) 2.00 kg of saccharose/starch pellets having a particle size between 0.500 and 0.710 mm are put in rotation in a suitable coating pan. The rotating mass is sprayed with 27.2 g of an ethanolic solution containing 9.79 g of shellac and 1.09 g of methylcellulose and 80 g of diltiazem HCl are added. This operation is repeated 50 times. Release data at varying pH values is shown in FIG. 11.

b.10) 2.00 kg of saccharose/starch pellets having a particle size between 0.500 and 0.710 mm are put in rotation in a suitable coating pan. The rotating mass is sprayed with 27.2 g of an ethanolic solution containing 7.52 g of shellac and 3.25 g of methylcellulose and 80 g of diltiazem HCl are added. This operation is repeated 50 times. Release data at varying pH values is shown in FIG. 12.

b.11) 2.00 kg of saccharose/starch pellets having a particle size between 0.500 and 0.710 mm are put in rotation in a suitable coating pan. The rotating mass is sprayed with 27.2 g of an ethanolic solution containing 5.44 g of shellac and 5.44 g of methylcellulose and 80 g of diltiazem HCl are added. This operation is repeated 50 times. Release data at varying pH values is shown in FIG. 13.

b.12) 2.00 kg of saccharose/starch pellets having a particle size between 0.500 and 0.710 mm are put in rotation in a suitable coating pan. The rotating mass is sprayed with 27.2 g of an ethanolic solution containing 3.26 g of shellac and 7.62 g of methylcellulose and 80 g of diltiazem HCl are added. This operation is repeated 50 times. Release data at varying pH values is shown in FIG. 14.

All the preparations have been subsequently coated with the same amount of solution of ethylcellulose N100 and talc, respectively 80 g of 0.5% solution of ethylcellulose N100 and 54 g of talc. This operation has been repeated 25 times.

All the formulations have been tested for in-vitro dissolution, in the range of pH between 1 and 7.5, using the method described in the USPXXI, paddle apparatus.

As shown by the in-vitro release curves, the addition of a binder with hydro-lipophilic properties like polyvinylpyrrolidone, improves the pH independence of the in-vitro release rates.

This effect is optimal for ratios of insoluble/soluble binders between 70 and 50%.

I claim:

1. A process for preparing a medication containing diltiazem-HCl consisting of:
   a. rotating an inert pellet of saccharose/starch in a coating apparatus;
   b. spraying the inert pellet with an ethanol solution consisting of diltiazem hydrochloride, ethanol, shellac as a water insoluble binder first component, and a binder second component exhibiting hydrophilic and lipophilic properties, the shellac as the water insoluble binder first component being present in a range of 36% to 12% by weight based upon the total amount of the ethanol solution, the binder second component exhibiting hydrophilic and lipophilic properties being selected from the group consisting of polyvinyl-pyrrolidone, polyethylene glycol, and methylcellulose and being present in the solution in a range of 4% to 28% by weight based upon the total amount of the ethanol solution, the amount of the shellac as the water insoluble binder first component exceeding the amount of binder second component exhibiting hydrophilic and lipophilic properties;
   c. repeating step b 40 to 70 times whereby there is obtained rapid release diltiazem pellets; and
   d. coating the rapid release diltiazem pellets with a solution consisting of ethylcellulose and talc; and
   e. repeating coating step d. 25 times whereby coated delayed-release diltiazem pellets are obtained.

2. The process according to claim 1 wherein the binder having hydro-lipophilic properties functions to render the dissolution kinetic of ditiazem HCl independent of pH.

3. A medication containing diltiazem-HCl produced according to a process consisting of:
   a. rotating an inert pellet of saccharose/starch in a coating apparatus;
   b. spraying the inert pellet with an ethanol solution consisting of diltiazem hydrochloride ethanol, shellac as a water insoluble binder first component and a binder second component exhibiting hydrophilic and lipophilic properties, the shellac as the water insoluble binder component being present in a range of 36% to 12% by weight based upon the total amount of the ethanol solution, the binder second component exhibiting hydrophilic and lipophilic properties being selected from the group consisting of polyvinyl-pyrrolidone, polyethylene glycol, and methylcellulose and being present in the solution in a range of 4% to 28% by weight based upon the total amount of the ethanol solution, the amount of shellac and the water insoluble binder first component exceeding the amount of binder second component exhibiting hydrophilic and lipophilic properties;
   c. repeating step b 40 to 70 times whereby there is obtained rapid release diltiazem pellets; and
   d. coating the rapid release diltiazem pellets with a solution consisting of ethylcellulose and talc; and
   e. repeating coating step d. 25 times.

4. The medication of claim 3 whereby the medication is in the form of solid, oral form, gelatin capsules.

* * * * *